(12) United States Patent
Zhao et al.

(10) Patent No.: US 9,440,921 B2
(45) Date of Patent: Sep. 13, 2016

(54) 3-N-BUTYL-1-ISOINDOLINONE AND USE THEREOF FOR PREVENTING OR TREATING CEREBRAL INFARCTION

(71) Applicants: SUN YAT-SEN UNIVERSITY, Guangzhou (CN); Chunshun Zhao, Guangzhou (CN)

(72) Inventors: Chunshun Zhao, Guangzhou (CN); Wenkai Xu, Guangzhou (CN)

(73) Assignees: SUN YAT-SEN UNIVERSITY, Guangzhou (CN); Chunshun Zhao, Guangzhou (CN)

( * ) Notice: Subject to any disclaimer, the term of this patent is extended or adjusted under 35 U.S.C. 154(b) by 0 days.

(21) Appl. No.: 14/658,270

(22) Filed: Mar. 16, 2015

(65) Prior Publication Data

US 2015/0183738 A1    Jul. 2, 2015

Related U.S. Application Data

(63) Continuation-in-part of application No. PCT/CN2013/083237, filed on Sep. 10, 2013.

(30) Foreign Application Priority Data

Sep. 14, 2012 (CN) .......................... 2012 1 0341648

(51) Int. Cl.
*C07D 209/46* (2006.01)

(52) U.S. Cl.
CPC .................. *C07D 209/46* (2013.01)

(58) Field of Classification Search
CPC ................................... C07D 209/46
See application file for complete search history.

(56) References Cited

FOREIGN PATENT DOCUMENTS

CN 101029037 A 9/2007
EP 1679070 A1 7/2006

OTHER PUBLICATIONS

Ruan, et al. Document No. 141:306610, retrieved from CAPLUS, entered in STN on Jul. 5, 2004.*
M. W. Chen et al., Asymmetric hydrogenolysis of racemic tertiary alcohols, 3-substituted 3-hydroxyisoindolin-1-ones, Chemical Communications, 2012, pp. 1698-1700, vol. 48, The Royal Society of Chemistry, United Kingdom.
E C. Wang et al., A new synthesis of 3-alkyl-1-isoindolinones, Tetrahedron Letters, 2002, pp. 9163-9165, vol. 43, Elsevier, United Kingdom.
M. D. Chen et al., A versatile approach for the asymmetric synthesis of 3-alkyl-2,3-dihydro-1H-isoindolin-1-ones, Tetrahedron, 2004, pp. 1651-1657, vol. 60, Elsevier, United Kingdom.
J. M. Chapman et al., Hypolipidemic activity of phthalimide derivatives V: reduced and hydrolytic products of simple cyclic imides, Journal of Pharmaceutical Sciences, 1984, pp. 1482-1484, vol. 73, No. 10, American Pharmacists Association, United States.

* cited by examiner

*Primary Examiner* — Shawquia Jackson
(74) *Attorney, Agent, or Firm* — Matthias Scholl, PC; Matthias Scholl (57) ABSTRACT

3-n-Butyl-1-isoindolinone and use thereof for preventing or treating cerebral infarction. The compound is prepared by: 1) employing phthalimide as a starting reactant, contacting a nucleophilic Grignard reagent with the original reactant to add an alkyl group to a carbonyl carbon of an amide bond of the original reactant, thus yielding an intermediate; and 2) removing an oxygen atom connected to a third carbon atom of the intermediate in the presence of boron trifluoride diethyl etherate as a catalyst and triethylsilane as a reductant.

8 Claims, 7 Drawing Sheets

3-N-BUTYL-1-ISOINDOLINONE AND USE THEREOF FOR PREVENTING OR TREATING CEREBRAL INFARCTION

CROSS-REFERENCE TO RELATED APPLICATIONS

This application is a continuation-in-part of International Patent Application No. PCT/CN2013/083237 with an international filing date of Sep. 10, 2013, designating the United States, now pending, and further claims priority benefits to Chinese Patent Application No. 201210341648.6 filed Sep. 14, 2012. The contents of all of the aforementioned applications, including any intervening amendments thereto, are incorporated herein by reference. Inquiries from the public to applicants or assignees concerning this document or the related applications should be directed to: Matthias Scholl P. C., Attn.: Dr. Matthias Scholl Esq., 245 First Street, 18th Floor, Cambridge, Mass. 02142.

BACKGROUND OF THE INVENTION

1. Field of the Invention

The invention belongs to 3-n-butyl-1-isoindolinone and the use thereof in preparation of drugs for preventing or treating cerebral infarction.

2. Description of the Related Art

Cerebral infarction (CI), also known as cerebral ischemic stroke (CIS), refers to the softening and necrosis of local brain tissue resulting from blood circulation disorders, ischemia, and hypoxia.

Butylphthalide is one multi-target anti-cerebral ischemia drug, and studies have shown that butylphthalide has therapeutic effectiveness for preventing and treating CI. However, butylphthalide is an oily liquid and is water insoluble; as a result, it can only be prepared in the form of oil-soluble liquid preparations, which seriously limits the applications thereof.

SUMMARY OF THE INVENTION

The invention provides 3-n-butyl-1-isoindolinone obtained as a white crystalline solid which meets the requirements for preparing different dosage forms.

3-n-butyl-1-isoindolinone is useful for treating CI caused by local cerebral ischemia and its treatment efficacy is comparable to butylphthalide. Thus, 3-n-butyl-1-isoindolinone is efficacious for treating cerebral ischemia as well as overcomes the shortcomings of butylphthalide preparations.

To overcome the problems associated with the use of butylphthalide, it is one objective of the invention to provide 3-n-butyl-1-isoindolinone represented by formula I for preventing or treating cerebral ischemia. Because 3-n-butyl-1-isoindolinone has a structure of a crystalline solid, the compound has a broad selective range in dosage forms, thereby overcoming limitations of butylphthalide in preparation aspects and has great significance in industrial production and decreasing the medicine cost.

To achieve the above objective, in accordance with one embodiment of the invention, there is provided a compound represented by formula I, Formula I In certain embodiments of the invention, 3-n-butyl-1-isoindolinone is prepared by the following process: 1) employing phthalimide as a starting reactant, contacting a nucleophilic Grignard reagent with the original reactant to add an alkyl group to a carbonyl carbon of an amide bond of the original reactant, whereby yielding an intermediate; and 2) removing an oxygen atom connected to a third carbon atom of the intermediate in the presence of boron trifluoride diethyl etherate as a catalyst and triethylsilane as a reductant, whereby obtaining a deoxidized product.

In a class of this embodiment, the nucleophilic Grignard reagent is butyl magnesium bromide or butyl magnesium chloride.

The invention also provides a method for preventing or treating cerebral infarction comprising administering to a patient suffering from cerebral infarction 3-n-butyl-1-isoindolinone represented by formula I.

Studies show that compared with 3-n-butylphthalide, 3-n-butyl-1-isoindolinone has no statistical difference in treating CIS.

The term 3-n-butyl-1-isoindolinone is meant to encompass: (±) 3-n-butyl-1-isoindolinone, (+) 3-n-butyl-1-isoindolinone, and (−) 3-n-butyl-1-isoindolinone.

The middle cerebral artery occlusion (MCAO) model in rats is constructed to observe the anti-cerebral ischemia of 3-n-butyl-1-isoindolinone. The MCAO model is divided into three groups: 1) a negative control group, i.e., an vegetable oil, 3 mL/kg; 2) 3-n-butyl-1-isoindolinone group, 30 mg/kg; 3) a positive control group, i.e., 3-n-butylphthalide, 30 mg/kg. All the three groups are administered via intraperitoneal injection. Male SD rats having a weight of 250 g are selected and administered 15 min after the ischemia. After 2 hrs of cerebral infarction and 24 hrs of reperfusion, brain slices are prepared and conducted with TTC staining. Software image J is used to process staining results, calculate infarct areas, and compared with the results among different groups. It is known from the results that an average infarct area of the blank group is 24.430%, the average infarct area of the 3-n-butyl-1-isoindolinone group is 14.365%, and the average infarct area of the butylphthalide group is 14.402%. Statistic results indicate that 3-n-butyl-1-isoindolinone has no significant statistical difference in efficacy of treating cerebral ischemia compared with butylphthalide.

The results of the invention prove that 3-n-butyl-1-isoindolinone has good efficacy in treating cerebral ischemia. Besides, compared with the oily liquid structure of butylphthalide, the crystalline solid structure of 3-n-butyl-1-isoindolinone provides a broader selective range in the preparation field, provides possibility for changing the administration ways, and is beneficial for decreasing the pharmaceutical cost and improving the drug efficiency. Thus, 3-n-butyl-1-isoindolinone has great application prospect.

The invention further provides a pharmaceutical composition comprising 3-n-butyl-1-isoindolinone as an active component and a pharmaceutically acceptable excipient or adjunct. Generally the pharmaceutical composition contains between 0.1 and 95 wt. % of 3-n-butyl isoindolinone.

The pharmaceutical composition can be prepared using well known methods in the technical field. For such purpose, 3-n-butyl-1-isoindolinone is adapted to mix with one or a plurality of solid or liquid drug excipients and/or adjuncts if necessary, whereby preparing drugs for human or animals in proper administration forms or dosage forms.

In the preparation aspects, because 3-n-butyl-1-isoindolinone is in the crystal morphology, 3-n-butyl-1-isoindolinone or the pharmaceutical composition comprising the compound can be made into liquid dosage forms, gas dosage forms, semisolid dosage forms, and solid dosage forms. For example, the liquid dosage forms comprise: true solutions, emulsion dosage forms, suspension dosage forms, particle dosage forms, and colloid dosage form. The gas dosage forms comprise: aerosols, sprays, and dry powder inhalations. The semisolid dosage forms comprise: oral pastes, externally used pastes, and pastes. The solid dosage forms comprise: tablets, capsules, dropping pills, pills, powder, suppositories, granules, freeze-dried powder, and the like.

3-n-butyl-1-isoindolinone and the pharmaceutical composition comprising the same are administered in the form of the unit dose. The administration is accomplished via enteral or parenteral routes, such as oral, intramuscular, subcutaneous, nasal, oral mucosa, skin, peritoneum, and rectum administrations.

Administration routes of 3-n-butyl-1-isoindolinone and the pharmaceutical composition comprising the same are applicable for injection administration, including intravenous injection, intramuscular injection, subcutaneous injection, intradermal injection, and acupoint injection.

3-n-butyl-1-isoindolinone and the pharmaceutical composition comprising the same are made into common preparations, or into sustained-release preparations, target dry delivery systems, and other particle delivery systems.

To make the unit dosage forms into tablets, a plurality of know carriers in the technical field can be widely used. The carries comprises: diluents and absorbents, such as starch, dextrin, calcium sulfate, lactose, mannitol, sucrose, sodium chloride, glucose, urea, calcium carbonate, kaolin, microcrystalline cellulose, and aluminum silicate, etc.; wetting agents and adhesives, such as water, glycerol, polyethylene glycol, ethanol, propanol, starch paste, dextrin, syrup, honey, glucose solution, arabic gum, gelatin, carboxymethylcellulose sodium, shellac, methyl cellulose, potassium phosphate, and polyvinyl pyrrolidone, etc.; disintegrating agents, such as dried starch, alginate, agar powder, alginate starch, sodium bicarbonate and citric acid, calcium carbonate, polyoxyethylene sorbitan fatty acid esters, sodium dodecyl sulfonate, methylcellulose, and ethyl cellulose, etc.; disintegration inhibitors, such as sucrose, glycerol tristearate, cacao butter, hydrogenated oil, etc.; absorption accelerators, such as quaternary ammonium salts and sodium dodecyl sulfate, etc.; and lubricants, such as talc, silica, corn starch, stearic acid salts, boric acid, liquid paraffin, polyethylene glycol and the like. Tablets can also be made into coated tablets, such as sugar-coated tablets, film-coated tablets, enteric coated tablets, or double-layer tablets and multi-layer tablets.

For example, to make the unit dosage forms into pills, a plurality of known carriers in the technical field can be widely adopted. The carriers for pills comprise: diluents and absorbents, such as glucose, lactose, starch, cacao butter, hydrogenated vegetable oil, polyvinylpyrrolidone, kaolin, talc, etc.; adhesives, such as arabic gum, tragacanth, gelatin, ethanol, honey, liquid glucose, rice paste, or panada, etc.; and disintegrating agents, such as agar powder, dried starch, alginate, sodium dodecyl sulfonate, methylcellulose, and ethyl cellulose, etc.

For example, to make the unit dosage forms into capsules, the effective component 3-n-butyl-1-isoindolinone and the above carriers are mixed, and a resulting mixture are encapsulated into hard gelatin capsules or soft capsules. Or, the effective component 3-n-butyl-1-isoindolinone are made into microcapsules and suspended in aqueous solutions to form suspensions, or encapsulated into hard capsules, or be made into injections for application.

For example, to make the unit dosage forms into injection preparations, such as solutions, suspensions, emulsions, free-dried powder, such preparations can be aqueous or non-aqueous and comprise one and/or a plurality of pharmaceutically acceptable carriers, diluents, adhesives, lubricants, preservatives, surfactants, or dispersants. For example, the diluents can be selected from water, ethanol, polyethylene glycol, 1,3-propylene glycol, ethoxylated isostearyl alcohols, multi-oxidized isostearyl alcohols, and polyoxyethylene sorbitan fatty acid esters. Furthermore, to prepare isotonic injections, a proper dose of sodium chloride, glucose, or glycerol can be added to the injection preparations. Also, conventional cosolvents, buffers, pH adjusting agents can also be added. Such adjuncts are commonly used in the technical field.

In addition, colorants, preservatives, perfumes, flavoring agents, sweeteners, or other materials can be added to the drug preparations if necessary.

To achieve the administration purpose and enhance the treating efficacy, the drug or the pharmaceutical composition of the invention can be administered by any known methods.

The dose of the pharmaceutical composition comprising 3-n-butyl-1-isoindolinone is determined by a plurality of factors, for example, the nature and the severity of the disease to be prevented or treated, the gender, age, weight, temperament, and individual response of the patients or animals, the administration route, the administration times, and the treatment purpose. Thus, the therapeutic dose of the pharmaceutical composition may vary within a large range. Generally, doses of pharmaceutical ingredients are known by persons skilled in the art and can be properly adjusted according to the dose of the actual ingredients contained in the final preparation of the composition comprising 3-n-butyl-1-isoindolinone, thereby reaching the required effective amount for treatment and realizing the purpose for prevention or treatment. A proper dose of 3-n-butyl-1-isoindolinone is preferably between 0.1 and 100 mg per kg of weight per day, and more preferably 0.1-100 mg/day/person. The above dose can be in the form of a single dose forms or be divided into several, for example, two, three, or four dose forms, which is limited by clinical experience of doctors and other administration methods applying other treatment means.

A total dose required for each treatment can be divided into several times or once dose administration. The compound or the composition comprising the same can be administered alone, or administered along with other treating drugs or symptomatic drugs with adjusted doses.

The invention is described in detail hereinbelow combining with examples, and it should be noted that the following examples are not intended to limit the invention.

DETAILED DESCRIPTION OF THE EMBODIMENTS

For further illustrating the invention, experiments detailing 3-n-butyl-1-isoindolinone and the use thereof in preparation of drugs for preventing or treating cerebral infarction are described below. It should be noted that the following examples are intended to describe and not to limit the invention.

Example 1

Synthesis of 3-n-butyl-1-isoindolinone (NBI)

The objective product is obtained using Grignard reagent reduction method by two-step reaction. First, phthalimide is selected as a starting reactant, and a nucleophilic Grignard reagent, i.e., butyl magnesium bromide, is used to realize addition of an alkyl group of a carbonyl carbon of an amide bond, thereby yielding an intermediate. Second, boron trifluoride diethyl etherate is used as a catalyst and triethylsilane is used as a reductant to remove an oxygen atom from a third carbon atom, thereby obtaining a deoxidized product, i.e., NBI. The compound is purified by multiple times recrystallization, and structure of the compound is confirmed by mass spectrum (MS) and nuclear magnetic resonance ($^1$H-NMR, $^{13}$C-NMR). The synthesis flow chart of NBI is summarized as follows:

1. Preparation of Grignard Reagent Butyl Magnesium Bromide

Magnesium powder (approximately 0.240 g, 10 mmol) is accurately weighed and added to a dried 100 mL three-mouth flask. A dried magnetic stirrer and an iodine granule are subsequently added. The three-mouth flask is placed in a water bath. A middle mouth of the flask is connected to a dried condenser tube, and an upper end of the condenser tube is sealed with a rubber plug comprising a balloon. One side mouth of the flask is sealed with a rubber plug, and the other side mouth of the flask is connected to a pressure-equalizing dropping funnel N-butyl bromide (approximately 1.2 mL, 11 mmol) and 20 mL of anhydrous tetrahydrofuran are successively added via the pressure-equalizing dropping funnel. After that, connecting positions are examined to ensure sealed connections, the flask is then evacuated by a vacuum pump via the side mouth of the flask and then filled with nitrogen gas, and such processes are repeated for three times. The pressure-equalizing dropping funnel is opened, and approximately a half volume of N-butyl bromide (0.6 mL) is slowly dropped into the flask. The flask is allowed to stand, and a temperature of the water bath is regulated to be 38° C. As the stirring is slowly started, a large amount of bubbles are produced and a brown color of the solution fades. The pressure-equalizing dropping funnel is opened again, and remaining N-butyl bromide (0.6 mL) is dropped into the flask at a rate of one drop per second. After the dropping of the N-butyl bromide, the temperature of the water bath is regulated to 42° C., and refluxing is continued until the magnesium powder is completely dissolved.

2. Synthesis of 3-n-butyl-1-isoindolinone (NBI)

Reaction device of the Grignard reagent is taken out from the water bath and disposed on a thermostatic stirrer for ice bath. Phthalimide (1.471 g, 10 mmol) is accurately weighed and dissolved in anhydrous dichloromethane, and a resulting solution is dropped into butyl magnesium bromide while stirring via a pressure-equalizing dropping funnel, after approximately 3 hrs of reaction in the ice bath and anhydrous and anaerobic conditions, saturated ammonium chloride is added for quenching. The organic phase is separated by a separating funnel, and aqueous phase is extracted by dichloromethane for three times. The organic phases are combined, washed by a salt water, dried by anhydrous sodium sulfate, filtered, and concentrated by rotary evaporation, and thereafter separated by a silica gel column (petroleum ether:ethyl acetate=2:1), so that an intermediate a is yielded. A yield of the intermediate is 97 wt. %, and the intermediate is then dried in a vacuum drying oven.

The intermediate after being completely dried is dissolved in 20 mL of anhydrous dichloromethane in a round bottomed flask, and a dried stirrer is added. The flask is sealed by a rubber plug and filled with nitrogen gas for protection. The flask is then placed in a low-temperature reactor; an objective temperature is regulated to −15° C. When the temperature is decreased to the objective temperature, ten times molar volume of triethylsilane and three times molar volume of boron trifluoride diethyl etherate are successively added. The flask is transferred from the low-temperature reactor to a thermostatic magnetic stirrer, and reaction is conducted while stirring for overnight at a room temperature. After complete reaction, a saturated sodium bicarbonate is added to the flask to consume remaining reactants. The organic phase is separated and aqueous phase is extracted by dichloromethane for three times, and the organic phases are combined. The combined organic phase is then washed by a concentrated salt water, dried by anhydrous sodium sulfate, filtered, and vacuum concentrated. Separation is conducted using the silica gel column (petroleum ether:ethyl acetate=2:1), and white crystals, i.e., the final product NBI, are obtained, and the yield of NBI is 95 wt. %.

3. Structure Confirmation of 3-n-butyl-1-isoindolinone

Figure 1:
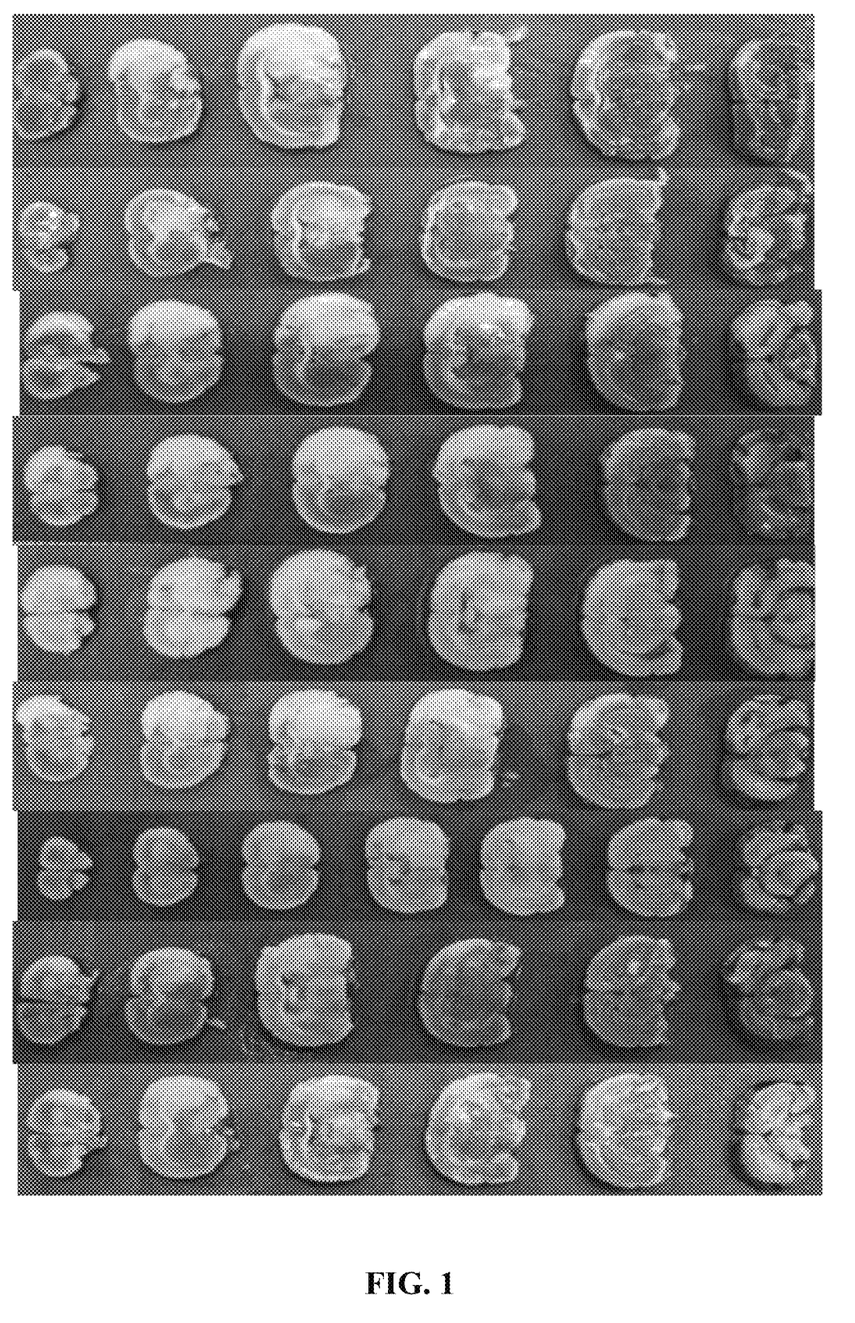
FIG. 1 is a digital picture showing staining results of brain slices of rats after 2 hrs of MCAO and 24 hrs of reperfusion in a blank control group.
Figure 2:
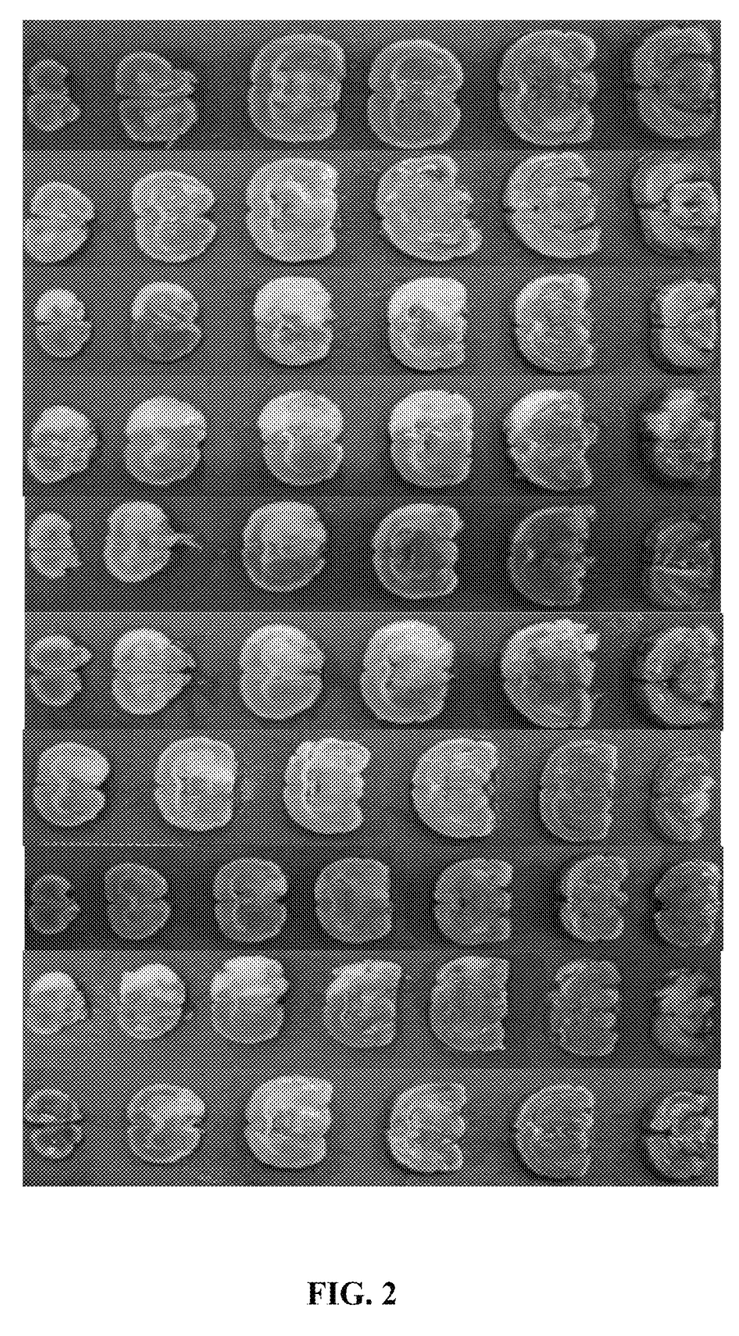
FIG. 2 is a digital picture showing staining results of brain slices of rats after 2 hrs of MCAO and 24 hrs of reperfusion in a 3-n-butyl-1-isoindolinone group.
Figure 3:
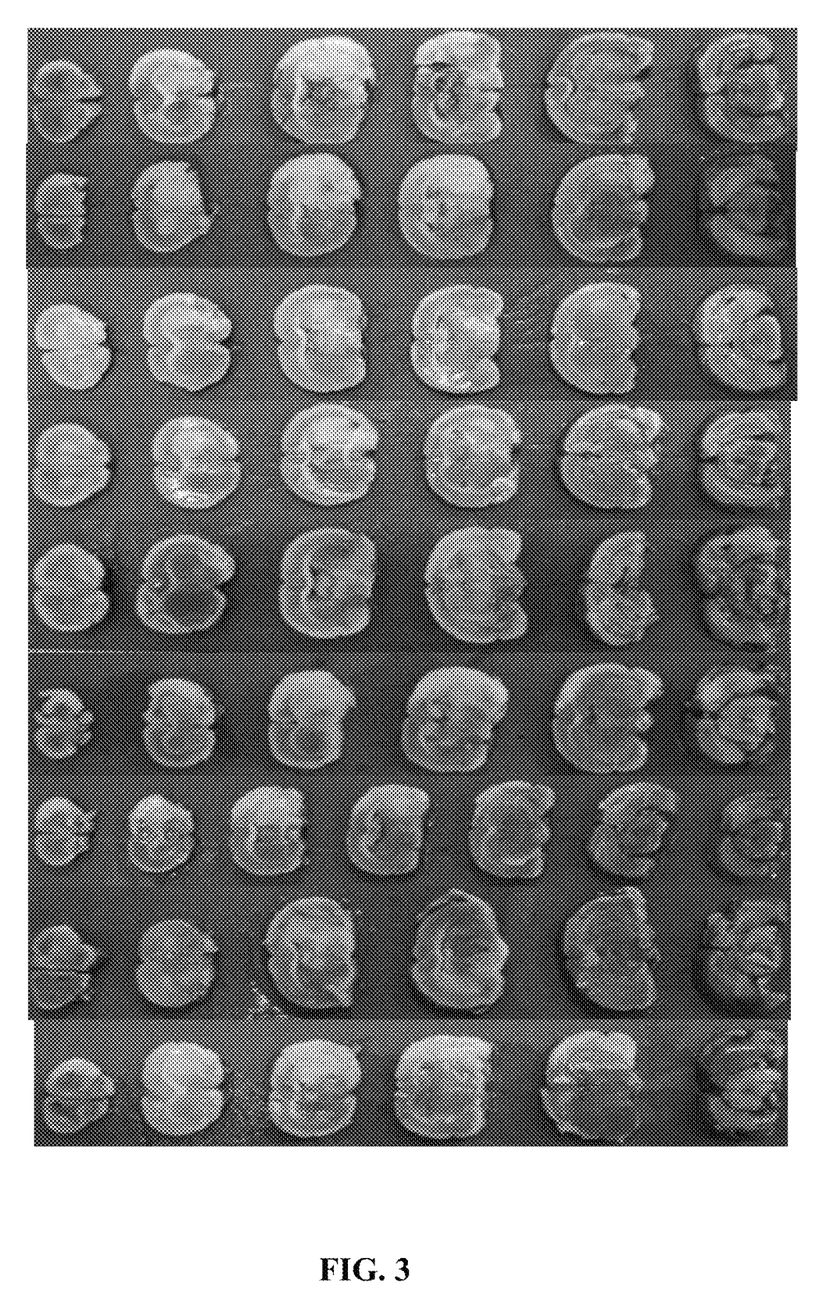
FIG. 3 is a digital picture showing staining results of brain slices of rats after 2 hrs of MCAO and 24 hrs of reperfusion in a butylphthalide group.
Figure 4:
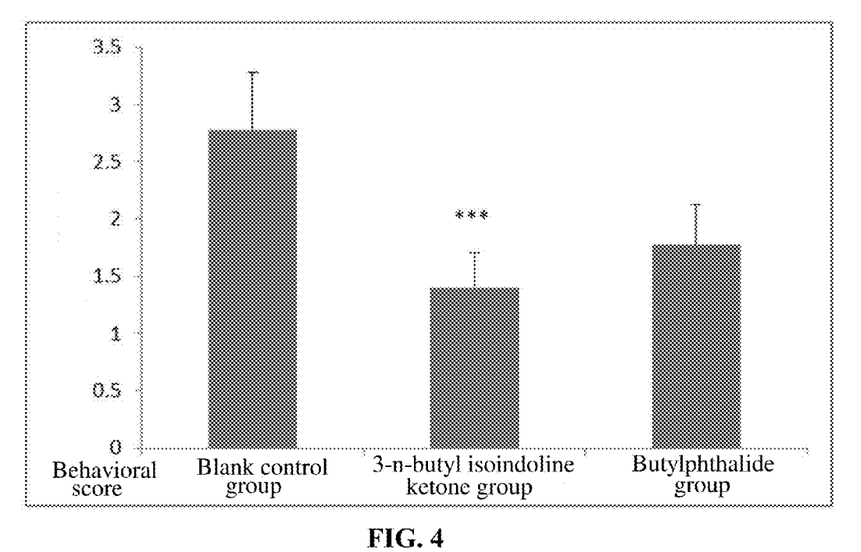
FIG. 4 is a block diagram showing behavioral scores of a blank control group, a 3-n-butyl-1-isoindolinone group, and a butylphthalide group.
Figure 5:
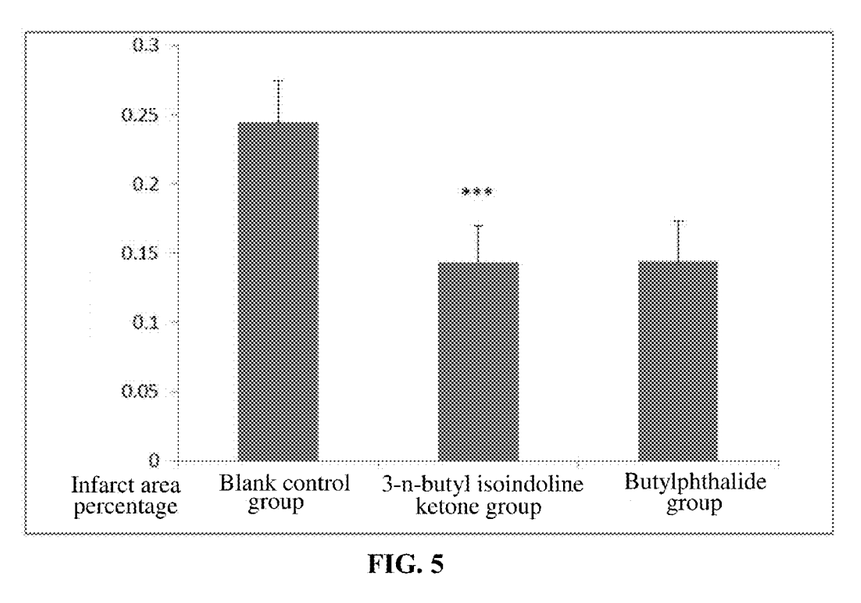
FIG. 5 is a block diagram showing infarct area percentages of a blank control group, a 3-n-butyl-1-isoindolinone group, and a butylphthalide group.
Figure 6:
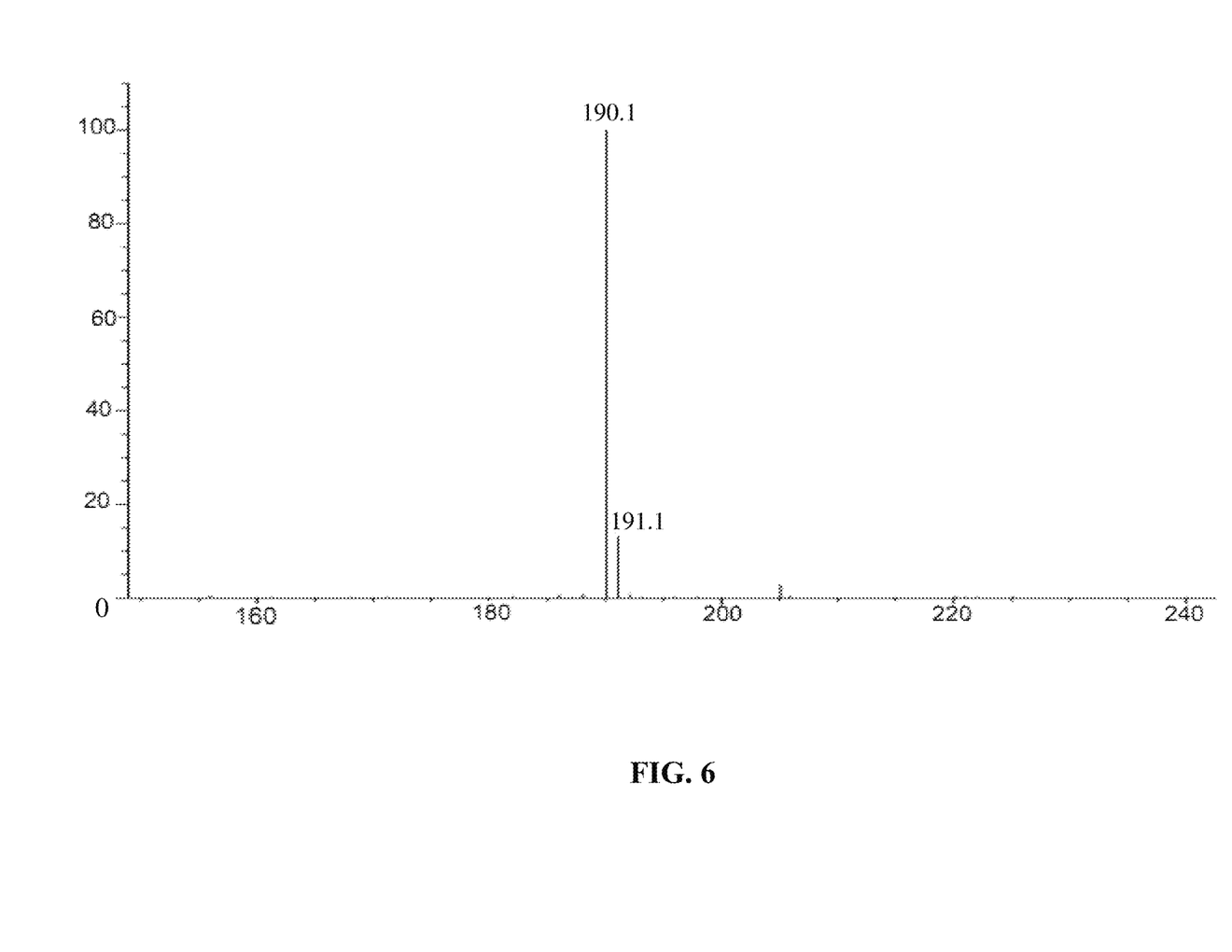
FIG. 6 is a mass spectrogram of NBI in accordance with one embodiment of the invention.
Figure 7:
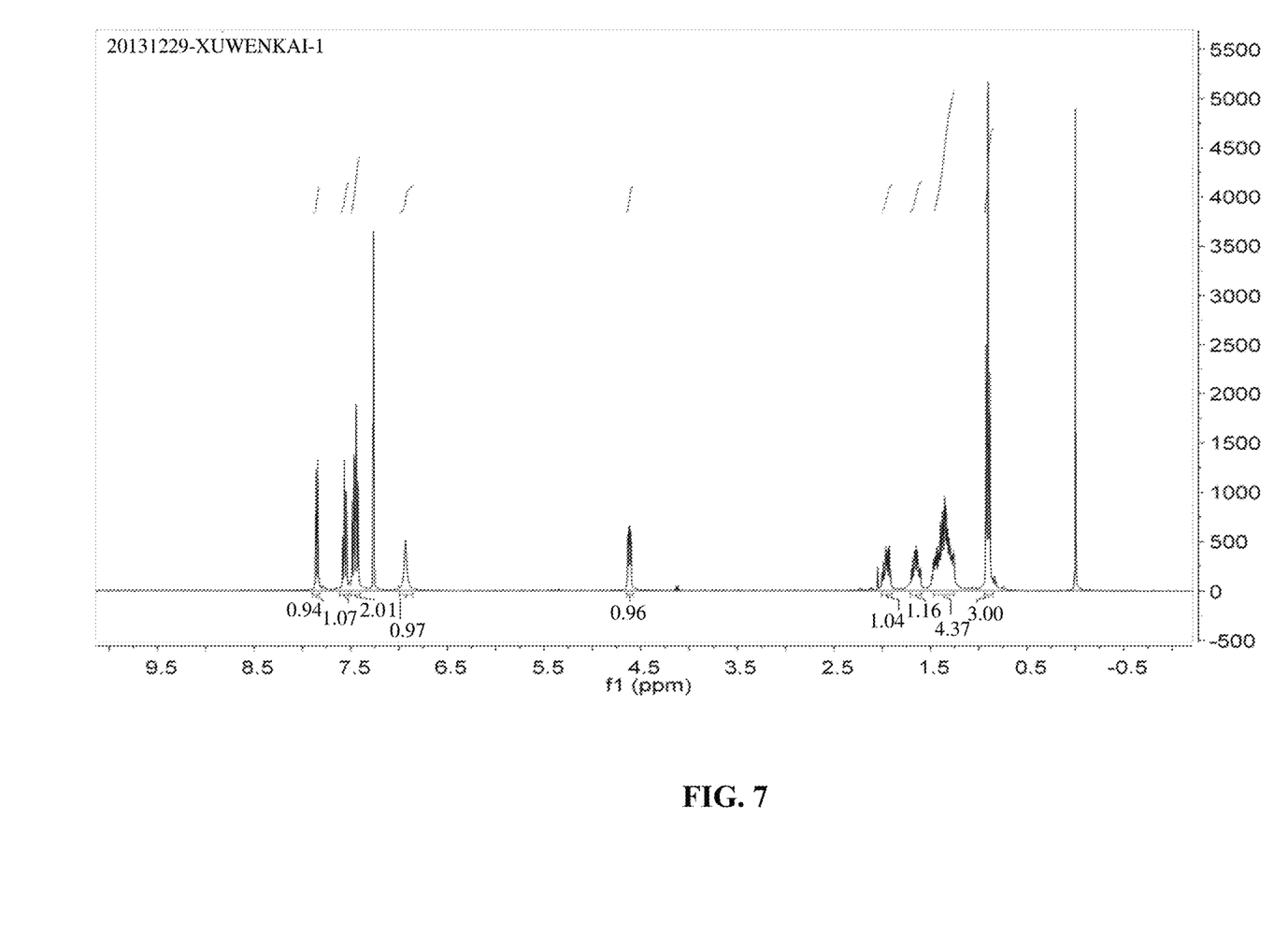
FIG. 7 is a $^1$H-NMR spectrum of NBI in accordance with one embodiment of the invention.
Figure 8:
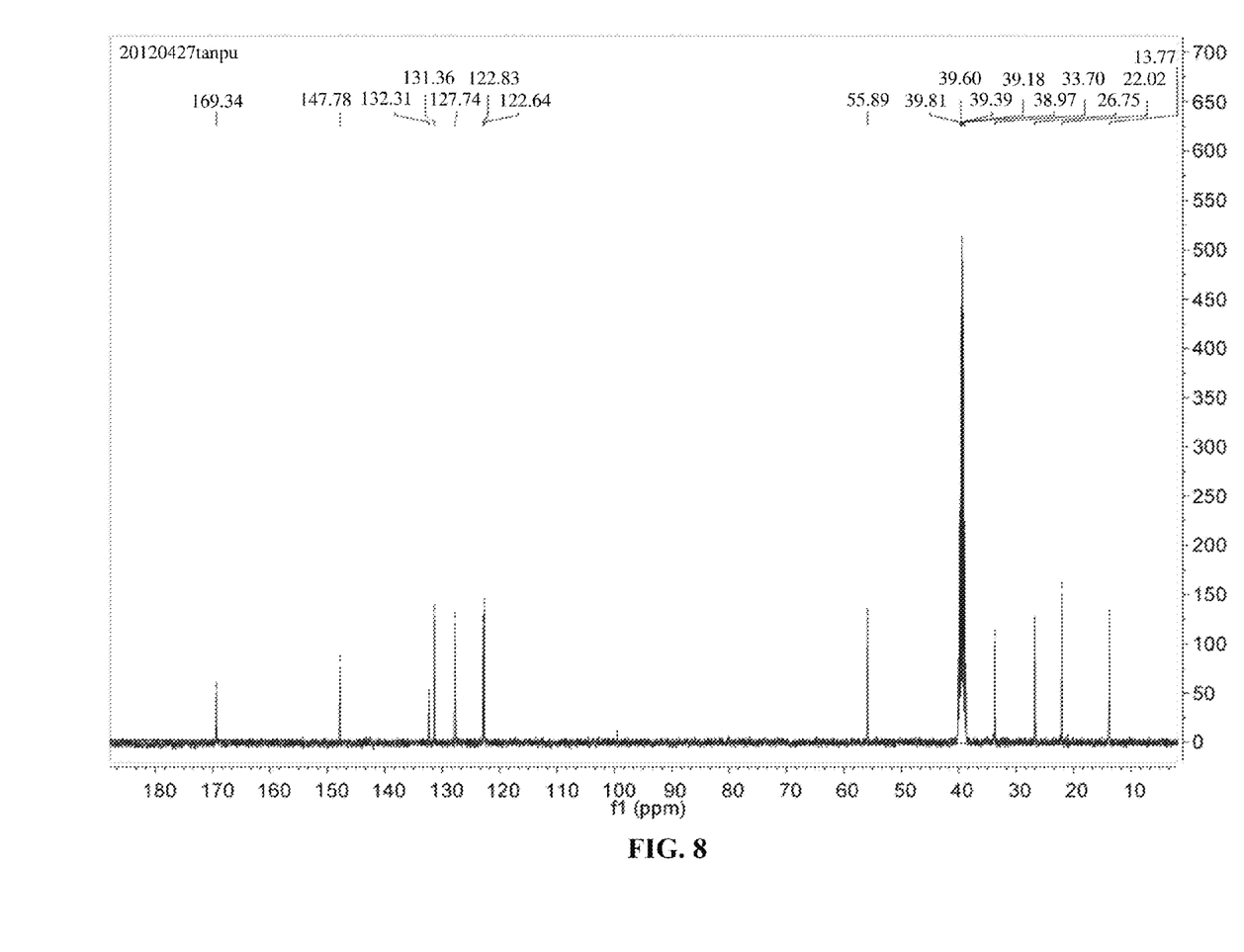
FIG. 8 is a $^{13}$C-NMR spectrum of NBI in accordance with one embodiment of the invention.

NBI is pure white crystals at the room temperature and has special odor and weak hygroscopicity. From the above reactions and purification by the silica gel column, the white crystals with slightly yellow are obtained. A small amount of the white crystals are collected and are characterized by mass spectrum (MS) and nuclear magnetic resonance ($^1$H-NMR, $^{13}$C-NMR), as shown in FIG. 1. Parameter results are as follows: MS (MM-ES+APCI, m/z): 190 (M+H$^+$, 100), 191[(M+2H)$^+$, 13]; $^1$H-NMR (400 MHz, CDCl$_3$) δ/ppm: 0.90 (t, 3H, CH$_3$), 1.32-1.39 (m, 4H, 2CH$_2$), 1.63-1.68 (m, 1H, CH$_2$Pr), 1.92-1.98 (m, 1H, CH$_2$Pr), 4.60-4.63 (dd, 1H, NCH), 6.93 (s, 1H, NH), 7.42-7.46 (m, 2H, Ar), 7.56 (m, 1H, Ar), 7.85 (d, 1H, Ar); $^{13}$C-NMR (100 MHz, deuteration DMSO) δ/ppm: 13.77 (CH3), 22.02 (CH2), 26.75 (CH2), 33.70 (CH2), 55.89 (CH), 122.64 (CH), 122.83 (CH), 127.74 (CH), 131.36 (CH), 132.31 (C), 147.78 (C), 169.34 (C).

In the synthesis process of NBI, the control of the anhydrous anaerobic condition has great influence on the yield of the final product. Only the anhydrous anaerobic condition is strictly controlled, the relatively high yield can be realized. Main reasons are as follows: 1. The covalent compound Grignard reagent is a very active organometallic reagent. The magnesium atom is directly connected to the carbon atom of the butyl group to form a polar covalent bond, and the carbon is the negatively charged terminal, thus, the Grignard reagent is a strong Lewis base capable of drawing electrons from water and other Lewis acid. If water and carbon dioxide exist in the reaction environment, a large amount of the Grignard reagent will be consumed, which seriously affects the yield of the objective product. 2. Both the complex boron trifluoride diethyl etherate and the active hydrogen donor triethylsilane are easily hydrolyzed. Thus, the whole reaction rout for the synthesis of NBI must be conducted in the anhydrous anaerobic condition, and certain requirements must also be satisfied on conditions of devices applied in subsequent pilot scale and industrialized production.

Example 2

Preparation of Tablets of 3-n-butyl-1-isoindolinone

| Prescription | |
|---|---|
| 3-n-butyl-1-isoindolinone | 20 g |
| Starch | 20 g |
| Ethanol (50 v. %) | proper amount |
| Sodium carboxymethyl starch | 3 g |
| magnesium stearate | 0.3 g |
| | 200 tablets |

3-n-butyl-1-isoindolinone is collected at an accurately constant weight according to the prescription, ground into powder, and screened by a 100-mesh sieve. Starch is collected at an accurately constant weight and screened by the 100-mesh sieve. 3-n-butyl-1-isoindolinone and starch after screening are evenly mixed, and a proper amount of 50 v. % of ethanol is added to a resulting mixture to prepare a damp mass. An 18-mesh nylon sieve is used for granulation. Granules are dried at a temperature of between 60 and 70° C. The 18-mesh sieve is then used for shaping the granules. After that, sodium carboxymethyl starch and magnesium stearate are added and evenly mixed. A ϕ8 mm press die is used to prepare tablets.

Example 3

Preparation of Hard Capsules of 3-n-butyl-1-isoindolinone

| Prescription | |
|---|---|
| 3-n-butyl-1-isoindolinone | 20 g |
| Starch | 20 g |
| Ethanol (50 v. %) | proper amount |
| Sodium carboxymethyl starch | 3 g |
| magnesium stearate | 0.3 g |
| | 200 capsules |

The wet granulation method herein is the same as that in Example 1. 3-n-butyl-1-isoindolinone is collected at an accurately constant weight according to the prescription, ground into powder, and screened by a 100-mesh sieve. Starch is collected at an accurately constant weight and screened by the 100-mesh sieve. 3-n-butyl-1-isoindolinone and starch after screening are evenly mixed, and a proper amount of 50 v. % of ethanol is added to a resulting mixture to prepare a damp mass. An 18-mesh nylon sieve is used for granulation. Granules are dried at a temperature of between 60 and 70° C. The 18-mesh sieve is used for shaping the granules. After that, contents of ingredients are measured, and qualified granules are encapsulated into number 1 capsules.

Example 4

Preparation of Soft Capsules of 3-n-butyl-1-isoindolinone 1 g of prepared 3-n-butyl-1-isoindolinone, 10 g of vegetable oil, 1 g of polyglycerol esters are collected and evenly mixed in a ball mill to prepare contents to be encapsulated in the soft capsules. Gelatin, glycerol, water, and opacifier at a ratio of 1:0.4:0.8:0.01 are collected as raw materials for making the capsules. Compression molding method is adopted to prepare the soft capsules. The soft capsules are solidified and dried by cool wind, and is washed and dried by suitable solvents, and 100 granules of the soft capsules are prepared.

Example 5

Preparation of Free-Dried Powder of 3-n-butyl-1-isoindolinone 1 g of prepared 3-n-butyl-1-isoindolinone is collected and dissolved in 800 mL of water for injection. 6 g of mannitol is then added. After full dissolution, the water for injection is added until a resulting solution reaches 1000 mL. The resulting solution is decarbonized by active carbon and is enabled to pass through a microporous membrane and then dispensed into 7 mL penicillin bottles with each bottle containing 4 mL. Bottle stoppers are then plugged in. The penicillin bottles are then free-dried and capped. A specification thereof is 4 mg of the free-dried powder of 3-n-butyl-1-isoindolinone for each bottle.

Example 6

Preparation of Injections of 3-n-butyl-1-isoindolinone 1 g of prepared 3-n-butyl-1-isoindolinone and 9 g of sodium chloride are added with 900 mL of water for injection, and a pH value of a resulting mixture is adjusted to be between 6.5 and 7.2. 3 g of needle carbon is added, evenly stirred, and boiled for 15 min. A resulting hot solution is filtered by a filter paper to remove the carbon and is finely filtered by a 0.22 µm microporous membrane. The water for injection is added until a resulting solution reaches 1000 mL. After that, a clarity of the solution is examined, and a qualified solution is dispensed into 5 mL ampoules. The ampoules are melt sealed and then pressure sterilized at the temperature of 110° C. for 30 min.

Example 7

Influence of 3-n-butyl-1-isoindolinone on Infarct Volume in MCAO Models of Rats

1) Construction of Middle Cerebral Artery Occlusion (MCAO) Models of Rats

Male SD rats having a weight of between 250 and 270 g are selected. The Male SD rats are cultivated at a room temperature of 25° C. and are forbidden from feeding food except for water 12 hrs before the operation. The MCAO models are constructed in accordance with longa method or the like. 10% chloral hydrate is used to anesthetize the rats by intraperitoneal injection with a dose of 350 mg/kg. The rat is then upwardly fixed on a rat plate in a supine position and illuminated by an incandescent lamp for maintaining a body temperature thereof at 37±0.5° C. Rat hairs at the middle position of the neck are sheared, and the skin at such position is incised after disinfection. The common carotid artery (CCA), external carotid artery (ECA), and internal carotid artery (ICA) of the right side are carefully separated. The ECA is cut, and a cut end is straightened and aligned with the ICA, and a thread is then inserted therefrom. The thread is inserted for a depth of approximately 19.0±0.5 mm. After 2 hrs, a part of the thread is pulled out to realize reperfusion. The rat after suture ligation is then put back to the rat cage. After 24 hrs of reperfusion, brain slices are prepared for staining.

2) Grouping and Administration

The rats are divided into three groups with 10 in each group: 1) a blank control group, i.e., an vegetable oil, 3 mL/kg; 2) 3-n-butyl-1-isoindolinone group, 30 mg/kg; 3) a positive control group, i.e., 3-n-butylphthalide, 30 mg/kg. All the three groups are administered with drugs via intraperitoneal injection 15 min after modeling.

3) Neurobehavioral Assessment

According to Zea Longa assessment, ethology observation is conducted after 2 hrs of modeling and 24 hrs of reperfusion and before killing the rats. The tail of the rat is seized to lift the rat about 1 foot off the ground to observe the condition of the left forelimb. The rat is placed on a flat ground, and the right and left shoulders of the rat are thrust from the right side and the left side, respectively, to compare the difference in resisting forces from the two sides. The rat is placed on the flat ground for free activities, and walking conditions of the rat are observed. The four-stage score method (scores of 0-5) is adopted, and the higher the score is, the more serious the neurobehavioral damage is.

1. If the behavior is completely normal, record score of 0.
2. Lift the rat tail off the ground, if the rat pronates forelimb of an opposite side of the operation, record score of 1.
3. Place the rat on the ground, use hand to push the two sides thereof to exam the resisting forces, and if the resisting force from the opposite side of the operation decreases, record score of 2.
4. Place the rat on the ground and observe its walking, and if the rat circles around the opposite side of the operation, record score of 3.
5. If the damage is very serious, the rat is unable to perform any independent activities, record score of 4.

The higher the score is, the more serious the cerebral damage is resulted, herein too slight or too serious of the damage cannot be chosen as the final test model. A standard modeling satisfies that the result of the neurobehavioral assessment 2 hrs after the modeling and before pulling out of the thread is score of 3, i.e., obvious circling behaviors can be observed.

After 24 hrs of reperfusion of the MCAO models of the rats, the neurobehavioral assessment is conducted on the rats again, and the results are recorded.

4) Measurement and Calculation of Cerebral Infarct Area

After 24 hrs of reperfusion, brains are collected from killed rats and placed in Petri dishes. The brain tissues are quickly collected and placed in a refrigerator at a temperature of −20° C. for 20 min and taken out. The olfactory bulb, the cerebellum, and the lower brainstem are removed, and the remaining brain is then cut for five times with an interval of 2 mm, whereby six consecutive coronal brain slices are formed. 2% TTC dye solution is added to the Petri dishes to submerge the brain slice by the solution. The Petri dishes are placed at the temperature of 37° C. and incubated in the absence of light for between 25 and 30 min during which the brain slices are turned over once every 5 min. After TTC staining of the brain slices, a normal tissue thereof presents red and an ischemic region presents white. When the TTC staining is finished, the TTC dye solution is removed out of the Petri dishes by syringes. Formalin solution with an amount enabling to submerge the brain slices is then added, and the Petri dishes are placed in the dark. After 24 hrs, solidified brain slices are taken out and arranged in order in a blue background to take pictures. Image analysis system software image J is used to process the pictures, and an infarct area and a total area of the brain slice are calculated, respectively, and the cerebral infarct percentage is further derived using the equation: cerebral infarct percentage (%)= (infarct area/total area of brain slice)×100%. Because each slice has the same thickness of 2 mm, the infarct area is capable of representing the infarct volume to a certain degree.

5) Experiment Results

It is known from the results of the neurobehavioral assessment that in the solvent control group, rats recorded the score of 0 do not exist while rats recorded the score of 2 or score of 3 are predominant. Those rats that pronate the forelimbs when being lifted and present decreased resisting forces on the opposite side of the opposition in facing external thrusting forces are recorded the score of 2. Those rats presenting circling behavior are recorded the score of 3. Some rats that present relatively serious symptoms and are paralyzed on the ground are recorded the score of 4. Experiment data are linearly processed by the statistical software SPSS 17.0 and one-factor analysis of variance (ANOVA) is used to exam neurobehavioral differences among groups, which indicates that the 3-n-butyl-1-isoindolinone group has significant difference (P=0.003<0.01) in alleviation of the neurobehavior compared with the blank control group and has no significant difference (P=0.384>0.05) compared with the butylphthalide group, and that the butylphthalide group has significant difference in alleviation of the neurobehavior compared with the blank control group (P=0.031<0.05). It is proved from the results of the neurobehavioral assessment that the 3-n-butyl-1-isoindolinone has a certain efficacy in alleviating symptoms caused by local cerebral ischemia in rats, and the alleviating efficacy of 3-n-butyl-1-isoindolinone is even slightly better than that of butylphthalide. This conclusion is coincident with the staining results of the brain slices, and further indicates that the improvement in the drug efficacy on the neurobehavior is in parallel correlation with the effect of reducing the infarct area.

The influence of 3-n-butyl-1-isoindolinone on the cerebral infarct volume is illustrated in accompanying pictures of the experiment results.

The infarct area and the total area of the slices of all the groups are collected by image J to calculate the infarct percentage. The statistical software SPSS 17.0 is used to process the data results and it is proved that the efficacy of 3-n-butyl-1-isoindolinone for reducing the infarct region is very obvious and is even better than the butylphthalide positive control group. Compared with the solvent control group, the infarct volume of the 3-n-butyl-1-isoindolinone group is reduced by 41.199%, thereby presenting an obvious effect. The effects of reduction of the infarct regions of the three groups are compared using the one-factor ANOVA method, and it is indicated from the comparisons that the 3-n-butyl-1-isoindolinone group has significant difference (P<0.001) in the reduced infarct area compared with the blank control group, and the difference between the 3-n-butyl-1-isoindolinone group and the butylphthalide has no statistical significance (P=0.989). Butylphthalide also has significant difference (P<0.01) in the reduced infarct area compared with the blank control group.

The above results prove that 3-n-butyl-1-isoindolinone has a certain therapeutic effect on the ischemia cerebral infarction and has great significance in treating the clinical cerebral infarction.

While particular embodiments of the invention have been shown and described, it will be obvious to those skilled in the art that changes and modifications may be made without departing from the invention in its broader aspects, and therefore, the aim in the appended claims is to cover all such changes and modifications as fall within the true spirit and scope of the invention.

The invention claimed is:

1. A method for preparing 3-n-alkyl-1-isoindolinone, comprising: 1) employing phthalimide as a starting material, contacting a nucleophilic Grignard reagent with the original reactant to add an alkyl group to a carbonyl carbon of an amide bond of the original reactant, whereby yielding an intermediate; and 2) removing an oxygen atom connected to a third carbon atom of the intermediate in the presence of boron trifluoride diethyl etherate as a catalyst and triethylsilane as a reductant, whereby obtaining 3-n-butyl-1-isoindolinone.

2. The method of claim 1, wherein the nucleophilic Grignard reagent is butyl magnesium bromide or butyl magnesium chloride.

3. A method for preventing or treating cerebral infarction comprising administering to a patient suffering from a cerebral infarction 3-n-butyl-1-isoindolinone or a pharmaceutical composition comprising 3-n-butyl-1-isoindolinone and a pharmaceutically-acceptable excipient.

4. The method of claim 3, wherein 3-n-butyl-1-isoindolinone is (±) 3-n-butyl-1-isoindolinone, (+) 3-n-butyl-1-isoindolinone, or (−) 3-n-butyl-1-isoindolinone.

5. The method of claim 3, wherein the cerebral infarction is caused by local ischemia.

6. The method of claim 3, wherein a therapeutically effective dose of the compound is between 0.1 and 100 mg per kg of body weight of the patient per day.

7. A pharmaceutical composition, comprising:
   a) a therapeutically effective dose of 3-n-butyl-1-isoindolinone; and
   b) a pharmaceutically acceptable carrier or an excipient.

8. The pharmaceutical composition of claim 7, wherein the pharmaceutical composition is prepared as a dosage form selected from tablets, capsules, injections, granules, pills, powders, sustained-release preparations, modified-release preparations, and particle delivery systems.

* * * * *